United States Patent [19]
Gorsek

[11] Patent Number: 6,103,756
[45] Date of Patent: Aug. 15, 2000

[54] OCULAR ORALLY INGESTED COMPOSITION FOR PREVENTION AND TREATMENT OF INDIVIDUALS

[75] Inventor: Wayne F. Gorsek, Springfield, Ill.

[73] Assignee: VitaCost Inc., Springfield, Ill.

[21] Appl. No.: 09/372,055

[22] Filed: Aug. 11, 1999

[51] Int. Cl.⁷ .......................... A61K 31/355; A61K 31/07
[52] U.S. Cl. .......................... 514/458; 514/474; 514/725; 514/912; 514/913
[58] Field of Search .................................... 514/458, 474, 514/725, 912, 913

[56] References Cited

U.S. PATENT DOCUMENTS 5,688,828  11/1997  Helberg et al. .......................... 514/565

*Primary Examiner*—Zohreh Fay
*Attorney, Agent, or Firm*—Hoffman, Wasson & Gitler

[57] ABSTRACT

An ocular composition for prevention, stabilization, reversal and treatment of age related macular degeneration, cataracts, elevated ocular pressure, diabetic retinopathy and glaucoma.

3 Claims, No Drawings

OCULAR ORALLY INGESTED COMPOSITION FOR PREVENTION AND TREATMENT OF INDIVIDUALS

This application relates to a composition for the prevention, stabilization, reversal and treatment of age related macular degeneration, cataracts, elevated ocular pressure, diabetic retinopathy and glaucoma. An orally ingested composition is provided which contains effective amounts of vitamins, minerals and extracts which have been demonstrated to provide unique health benefits. Human eyesight is one of the world's most delicate and sophisticated feats of engineering. The process by which we see is so complex that even the most talented scientists do not understand it completely. As we grow older, the parts involved in this process break down and wear out. Eyes become vulnerable to a host of diseases that can cruelly rob us of this gift, leading to the serious, debilitating degeneration, which can lead to blindness.

It is an object of the present invention to provide a unique formulation which stops these eye parts from wearing out and breaking down, thus resulting in strong and healthy eyes for a lifetime.

SUMMARY OF THE INVENTION

The key to the unique formulation is a combination of specific nutrients that help to protect and neutralize free radicals that may damage vision in the body. These nutrients, namely carotenoids such as Lycopene which is found in tomatoes and lutein which is found in spinach help protect the retina from oxidative damage initiated by the absorption of light. Vitamins A, C and E are important ingredients which protect against light induced damage. Vitamin A assists in night and color vision protection, alpha lipoic acids are powerful antioxidants and extremely beneficial as are Bilberry extracts which are standardized to 25% anthocyanosides and support the health of the eye and circulatory system by providing antioxidant activity, improved microcirculation and support healthy connective tissue formation. In addition, L-Taurine is an essential ingredient, an amino acid, uses a building block of all other amino acids and is found in the eye, heart muscle, white blood cells, skeletal muscle, and central nervous system. These are essential nutrients shown to have a powerful protective effect on the health of the eye. Good vision is an important result.

DETAILED DESCRIPTION OF THE INVENTION

Disclosed is an unique formulation that prevents, stabilizes, reverses and treats age related macular degeneration, cataracts, elevated ocular pressure, diabetic retinopathy and glaucoma. It is an overall benefit based upon an unique combination of vitamins, minerals and nutrients to assist in providing better vision for aged and young patients.

The formulation comprises, as essential ingredients: 100–6000 mg of Vitamin C; 100–2000 IU of Vitamin E (d-alpha tocopherol); 100–20000 IU of Vitamin A; 100–1000 mg of Magnesium; 100–3000 mg of L-Taurine; 50–600 mcg Selenium, 40–1000 mg of Bilberry extract; a natural fruit, with standardized 10–50% anthocyanosides; 6–100 mg Lutein extract; 6–100 mg Lycopene extract; 50–1000 mg alpha lipoic acid; 10–1000 mg Quercetin (bioflavonoid); 10–1000 mg Rutin (bioflavonoid); and 10–1000 mg of citrus bioflavonoids. These are essential ingredients which have been shown to have a powerful protective effect on the health of the eye.

In addition to these components, at least one compound selected from the group consisting of Vitamin D3, thiamine, riboflavin, niacin, Vitamin B6, folic acid, Vitamin B12, biotin, pantothenic acid, Calcium, Iodine, Zinc, Copper, Manganese, Chromium, Molybdenum, N-acetyl-cysteine, plant enzymes, biopene, malic acid, L-glycine, L-glutathione and Boron can be added in effective amounts. A particularly preferred formulation including various components are listed in Table 1. A serving size includes 6 capsules, if desired, and has proved to provide effective results. Vitamin A which is provided in natural form, as betatene, combines a complex of carotenoids found in fruit and vegetables which, as antioxidants, protects cells from free radical damage. Vitamin C is required for collagen formation, healthy strong blood vessels and joint health. Bioflavonoids are powerful antioxidants included to enhance Vitamin C. Natural Vitamin E is an effective antioxidant. Vitamins B6, B12 and folic acid, when applied, have been shown to promote healthy homocystene levels. Zinc is included when desired to support immune functions and has free radical scavenging. The formulations set forth in Table 1 are exemplary and not provided for limitation.

One skilled in the art can easily modify or change the formulation within the specific description to provide an unique desired product which falls within the scope of the claims.

TABLE 1

| Amount per six capsules | Potency | % DV |
| --- | --- | --- |
| Vitamin A [as natural carotenoids (15,000 IU) beta carotene, alpha carotene, lutein, zeaxanthin, cryptoxanthin, palmitate (2,5000 IU)] | 17,500 IU | 350% |
| Vitamin C (as calcium ascorbate) | 1.5 g | 1,667% |
| Vitamin D3 (as cholecalciferol) | 400 IU | 175% |
| Natural Vitamin E (as d-alpha tocopheryl succinate, gamma, delta and beta tocopheryls) | 500 IU | 1,700% |
| Thiamine (vitamin B1 HCl) | 50 mg | 3,333% |
| Riboflavin (vitamin B2) | 10 mg | 588% |
| Niacin (vitamin B3 as niacin amide, niacin) | 70 mg | 350% |
| Vitamin B6 (as pyridoxine HCl) | 50 mg | 2,500% |
| Folic Acid (as folacin) | 800 mcg | 200% |
| Vitamin B12 (as methyl cobalamin) | 500 mcg | 8,333% |
| Biotin | 300 mcg | 100% |
| Pantothenic Acid (vitamin B5 as d-caldium pantothenate) | 50 mg | 500% |
| Calcium (as citrate malate, calcium ascorbate) | 500 mg | 50% |
| Iodine (as kelp) | 75 mcg | 50% |
| Magnesium (as taurate) | 300 mg | 75% |
| Zinc (as L-monomethionine) | 25 mg | 166% |
| Selenium (as I-selenomethionine) | 200 mcg | 286% |
| Copper (as chelate) | 1 mg | 50% |
| Manganese (as chelate) | 2 mg | 100% |
| Chromium (as chromium polynicotinate) | 200 mcg | 167% |
| Molybdenum (as chelate) | 75 mcg | 100% |
| Bilberry Extract (*Vaccinium myrtillus*) (berry extract) (standardized to 25% anthocyanosides) | 160 mg | ** |
| Lutein Extract (Standardized 5% (10 mg) | 200 mg | ** |
| Lycopene Extract | 12 mg | ** |
| Alpha Lipoic Acid | 150 mg | ** |
| N-Acetyl-Cysteine | 200 mg | ** |
| Bioflavonoid (as quercetin) | 100 mg | ** |
| Bioflavonoid (as rutin) | 100 mg | ** |
| Bioflavonoid (as citrus) | 250 mg | ** |
| Plant Enzymes (as amylase, cellulase, protease, lipase and lactase) | 50 mg | ** |
| Black Pepper (pipe nigrum) (fruit extract) | 5 mg | ** |
| Malic Acid (as calcium citrate malate) | 325 mg | ** |
| Taurine (as magnesium taurate) | 900 mg | ** |
| L-Glycine | 100 mg | ** |

TABLE 1-continued

| Amount per six capsules | Potency | % DV |
|---|---|---|
| L-Glutathione | 10 mg | ** |
| Boron (as chelate) | 2 mg | ** |

**Daily Value Not Established
Other Ingredients: Kosher Gelatin (capsule)
Please note: 1,000 mcg (microgram) = 1 mg (milligram)
1,000 mg = 1 g (gram)

What is claimed is:

1. An orally ingested composition for providing or treating macular degeneration, cataracts, elevated ocular pressure, diabetic retinopathy and glaucoma comprising:
    effective amounts of Vitamin A, Vitamin E, Vitamin C, Magnesium, Selenium, Bilberry extract, L-Taurine, Lutein extract, Lycopene extract, alpha lipoic acid, Quercetin, Rutin and Citrus Bioflavonoids.

2. The orally ingested composition of claim 1, further comprising:
    an effective amount of at least one compound selected from the group consisting of: Vitamin D3, Thiamine, Riboflavin, Niacin, Vitamin B6, Folic Acid, Vitamin B12, Biotin, Pantothenic Acid, Calcium, Iodine, Zinc, Copper, Manganese, Chromium, Molybdenum, n-Acetyl-cysteine, Plant Enzymes, Biopene, Malic Acid, L-Glycine, L-Glutathionine and Boron.

3. The orally ingested composition of claim 1, wherein the composition comprises:
    100–6000 mg Vitamin C; 100–2000 IU Vitamin E; 100–20000 IU Vitamin A; 100–1000 mg L-Taurine; 50–600 mcg Selenium; 40–1000 mg Bilberry extract; 6–100 mg Lutein extract; 6–100 mg Lycopene extract; 50–1000 mg alpha lipoic acid; 10–1000 mg Quercetin; 10–1000 mg Rutin and 10–1000 mg Citrus Bioflavonoids.

* * * * *